United States Patent
Stucki

(10) Patent No.: US 7,597,308 B1
(45) Date of Patent: Oct. 6, 2009

(54) CONSTANT-RATE VOLATILE MATERIAL DISPENSING DEVICE

(76) Inventor: Andre Stucki, 349 SE. 2$^{nd}$ Ave., Deerfield Beach, FL (US) 33441

( * ) Notice: Subject to any disclaimer, the term of this patent is extended or adjusted under 35 U.S.C. 154(b) by 362 days.

(21) Appl. No.: 11/786,287

(22) Filed: Apr. 11, 2007

Related U.S. Application Data

(60) Provisional application No. 60/791,133, filed on Apr. 11, 2006.

(51) Int. Cl.
*B01F 3/04* (2006.01)

(52) U.S. Cl. .......................... 261/30; 222/187; 261/71; 261/104; 261/DIG. 88

(58) Field of Classification Search .................. 261/30, 261/34.1, 37, 66, 71, 104, 107, DIG. 17, 261/DIG. 65, DIG. 88, DIG. 89; 239/53–56; 422/5, 28, 122–124; 222/3, 95, 96, 187
See application file for complete search history.

(56) References Cited

U.S. PATENT DOCUMENTS

| | | | | |
|---|---|---|---|---|
| 3,892,235 | A * | 7/1975 | Van Amerongen et al. | 128/200.16 |
| 3,982,095 | A * | 9/1976 | Robinson | 392/403 |
| 4,051,205 | A * | 9/1977 | Grant | 261/70 |
| 4,225,542 | A * | 9/1980 | Wall et al. | 261/142 |
| 4,288,396 | A * | 9/1981 | Ottestad | 261/128 |
| 4,367,182 | A * | 1/1983 | Kienholz | 261/124 |
| 4,461,735 | A * | 7/1984 | Wirt | 261/104 |
| 4,657,713 | A * | 4/1987 | Miller | 261/142 |
| 4,739,928 | A * | 4/1988 | O'Neil | 239/45 |
| 4,752,422 | A * | 6/1988 | Uchida et al. | 261/81 |
| 5,000,383 | A * | 3/1991 | van der Heijden | 239/47 |
| 5,238,187 | A * | 8/1993 | Zlotnik et al. | 239/6 |
| 5,247,604 | A * | 9/1993 | Chiu | 392/406 |
| 5,361,322 | A * | 11/1994 | Glucksman | 392/405 |
| 6,511,531 | B1 * | 1/2003 | Cartellone | 96/222 |
| 6,523,810 | B2 * | 2/2003 | Offir et al. | 261/72.1 |
| 6,869,065 | B1 * | 3/2005 | Lin | 261/3 |
| 7,040,548 | B2 * | 5/2006 | Rodgers | 239/34 |
| 2002/0158351 | A1 * | 10/2002 | Wohrle | 261/142 |
| 2004/0099967 | A1 * | 5/2004 | Chen | 261/66 |

FOREIGN PATENT DOCUMENTS

| | | | | | |
|---|---|---|---|---|---|
| JP | 54-98034 | A | * | 8/1979 | 261/DIG. 17 |
| JP | 5-52371 | A | * | 3/1993 | 261/DIG. 65 |

* cited by examiner

*Primary Examiner*—Richard L Chiesa
(74) *Attorney, Agent, or Firm*—Gold & Rizvi, P.A.; H. John Rizvi; Glenn E. Gold

(57) ABSTRACT

A volatile material dispensing device is provided, including a reservoir containing a supply of any one of numerous volatile materials having an outlet port with attached tube through which the volatile material flows, a valve and valve adjustment mechanism to control the flow rate through the tube, a lower housing incorporating a pad to receive the volatile material, and a tear-off tab that initially seals the tube and prevents flow until removed by the consumer. Optionally, the device may include an active mechanism, such as a fan, to aid dispersal of the volatile material. The device gives the user control of the intensity of the vapor by providing the ability to adjust the flow through the valve with the valve adjustment mechanism. The device also provides constant vapor intensity over time with a time-release dispersing mechanism delivering a controlled, consistent flow, with an appropriate drip rate.

20 Claims, 3 Drawing Sheets

CONSTANT-RATE VOLATILE MATERIAL DISPENSING DEVICE

CROSS-REFERENCE TO RELATED APPLICATION

This application claims the benefit of co-pending U.S. Provisional Patent Application Ser. No. 60/791,133, filed Apr. 11, 2006, which is incorporated herein in its entirety.

BACKGROUND OF THE INVENTION

1. Field of the Invention

The present invention relates generally to volatile material dispensing devices, and more particularly, to a volatile material dispensing device for dispensing at a constant rate.

2. Description of the Prior Art

A number of attempts have been made to devise volatile material dispensing devices. These devices dispense perfumed fluid, aromatic oils, odor deodorizers, disinfectants, scented gels, insecticides, or the like, that scent or modify the atmosphere. Typically these devices are used in a room, vehicle, or other confined space. Volatile material dispensing devices that are designed to produce a pleasing aroma, often called air fresheners, have become common household products. Not only do these provide a sense of cleanliness and pleasantness, but they also offer the benefit of increased safety. For example, some universities do not allow the use of candles in dormitory rooms due to the fire danger, but encourage the use of safe and effective volatile material air fresheners instead.

Various systems of dispersal are known, both active and passive.

Active systems include both manual systems and powered systems. Manual systems function when a button is pushed to activate the dispersal mechanism, such as when the button is depressed on an aerosol can. By quickly spraying a quantity of small particulates, manual systems have the advantage of fast delivery, however they do not provide automatic, continuous dispersal, but require the consumer's initiation each time dispensing is desired. Powered systems, using electricity or battery power, promote the diffusion of the vapor into the atmosphere by heating the volatile material, or by increasing air circulation and turbulence around the volatile material via a fan mechanism. Active powered systems, while automatically providing continuous dispersal, do not provide a constant level of intensity. They initially provide a higher intensity that diminishes as time passes, as demonstrated in FIG. 1. Even on the Glade® website, a popular manufacturer of electrically warmed scented oils, the FAQ page informs its customers to expect that the fragrance will be stronger the first few days.

Various passive types of volatile material dispensing devices are known. Some early types called inverted bottle evaporators used a gravity-fed system. A bottle filled with the liquid was inverted in a pan to allow a pool of the liquid to form in the pan. Evaporation occurred from the pool surrounding the neck of the bottle. This type was so prone to spills that it is no longer commercially available. Some other older types, which are still offered, employ a container of an aromatic liquid or oil that is open to the air. Often a wick is provided to increase the surface area available for evaporation. These too are messy, prone to spillage, and potentially hazardous to children and pets that might access the open container. Furthermore, the consumer cannot control the dispensing rate and the intensity fades over time. Aromatic gels or semi-solids were more recently introduced. Gels are often enclosed in a vapor-permeable material and formed into a convenient, disposable cartridge. Other disposable cartridges include pads or sponge-like material permeated with vaporizable agents. The cartridges are less cumbersome and more convenient, but the dispensing rate cannot be controlled and the scent is short lived, necessitating frequent replacement. Additionally, cartridges are not able to provide a constant level of intensity over time; instead the high initial intensity drops off quickly, as shown in FIG. 1.

Accordingly, there is an established need for a convenient volatile material dispensing device that is capable of delivering a controlled, consistent flow, producing a constant intensity of vapor over time.

SUMMARY OF THE INVENTION

The present invention is directed to an improved, effective, and easy to use volatile material dispensing device that is capable of delivering a controlled, consistent flow, with an appropriate drip rate to produce a constant intensity of vapor over time. The volatile material dispensing device includes a reservoir containing a supply of any one of numerous volatile materials having an outlet port with an attached tube through which the volatile material flows by gravity, a valve and valve adjustment mechanism to control the flow rate through the tube, and a lower housing that incorporates a pad to receive the volatile material. The volatile material dispensing device preferably includes a tear-off tab that initially seals the tube and prevents the flow of the volatile material until removed by the consumer to activate the system and initiate the flow. Optionally, the dispensing device may include an active mechanism, such as a fan, to aid dispersal of the volatile material. The dispensing device gives the user control of the intensity of the vapor by providing the ability to adjust the flow by utilizing the valve with the valve adjustment mechanism. The device also provides constant vapor intensity over time, as shown in FIG. 2, with a time-release dispersal mechanism delivering a controlled, consistent flow, with an appropriate drip rate.

An object of the present invention is to provide a volatile material dispensing device that allows for consistent dispersal of the volatile material to provide a constant intensity of vapor over time.

Another object of the present invention is to provide control of the amount of flow of the volatile material, thereby providing control of the quantity of the vapor released into the atmosphere.

An additional object of the present invention is to provide a controlled, consistent flow of the volatile material.

Another object of the present invention is to provide a volatile material dispensing device that is easy and economical to manufacture.

An additional object of the present invention is to provide a volatile material dispensing device that can be used in an existing fan type device as a replacement cartridge for other types of devices already on the market.

A further object of the present invention is to provide a volatile material dispensing device that can be adapted for use with a wide variety of volatile materials.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION OF THE PREFERRED EMBODIMENTS

Figure 1:
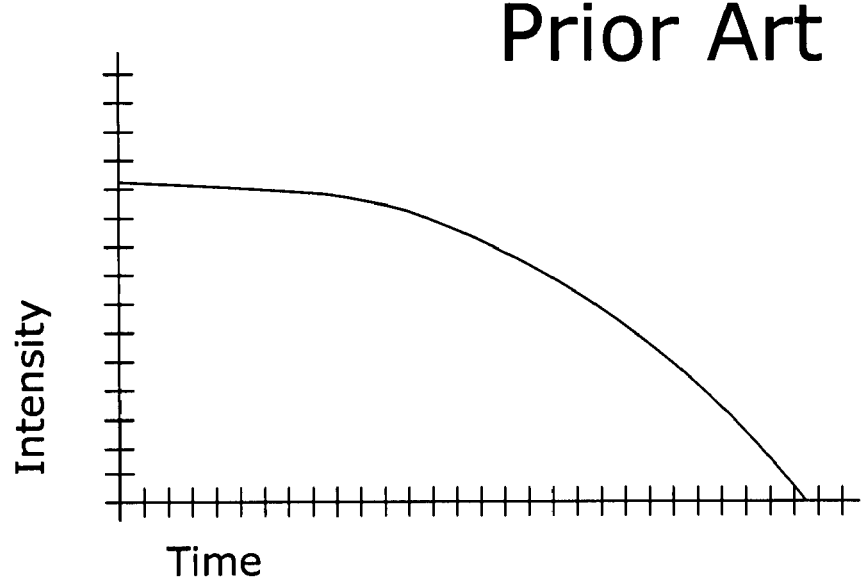
FIG. 1 is a graph demonstrating the varying, diminishing intensity of vapor release of prior art devices showing vapor intensity versus time.
Figure 2:
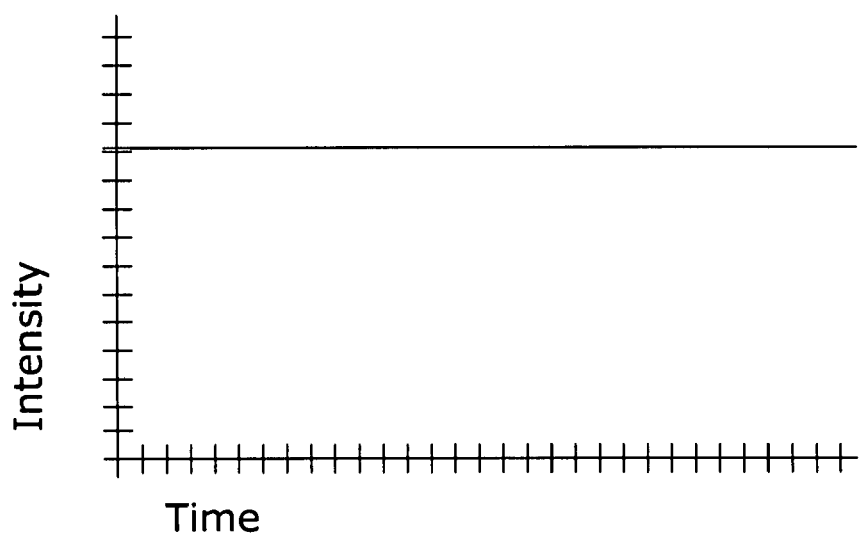
FIG. 2 is a graph demonstrating the constant intensity of vapor release of the volatile material dispensing device of the present invention showing vapor intensity versus time.

Shown throughout the figures, the present invention is directed towards an improved, effective, and easy to use volatile material dispensing device. Whereas previous devices exhibited a varying, decreasing vapor intensity over time as demonstrated in FIG. 1, the present improved volatile material dispensing device provides constant vapor intensity over time, as shown in FIG. 2, with a time-release dispensing mechanism delivering a controlled, consistent flow, with an appropriate drip rate.

Figure 3:
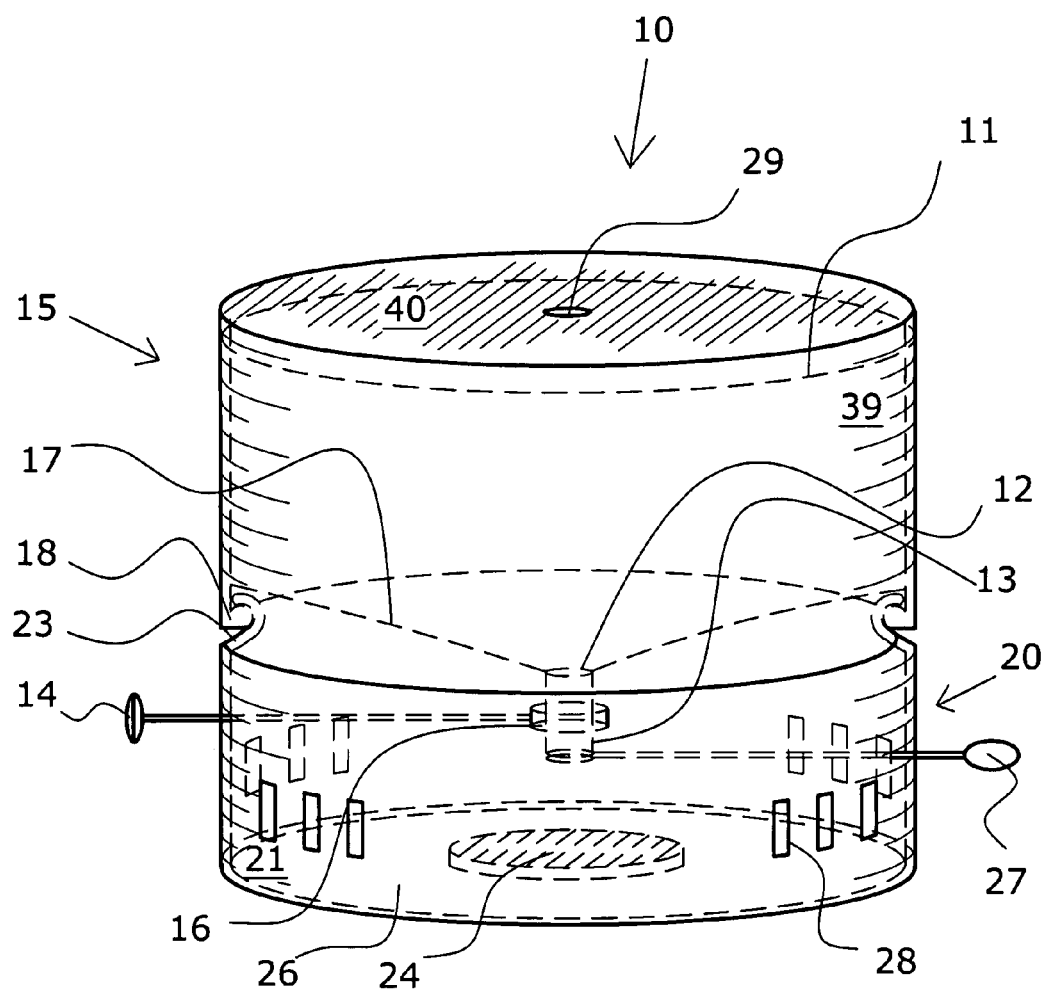
FIG. 3 is a perspective view showing a first preferred embodiment of the volatile material dispensing device of the present invention.

Referring now to FIG. 3, a volatile material dispensing device, shown generally as reference number 10, is illustrated in accordance with a preferred embodiment of the present invention. As shown, the volatile material dispensing device 10 comprises both an upper reservoir 15 and a lower housing 20, with a tube 13 fluidly connecting them.

Reservoir 15 comprises side wall 39, top 40, and bottom wall 41. The interior surface of reservoir 15 defines a cavity 17 that is designed to hold a supply of any of a number of volatile materials 11, such as perfumed fluid, aromatic oils, volatile organic compounds, aromatherapy scents, odor neutralizers, odor deodorizers, disinfectants, air fresheners, scented gels, insecticides, bioactive materials, or the like, that condition, modify, or otherwise change the atmosphere. A combination of more than one of these volatile materials 11 may optionally be utilized in the volatile material dispensing device of the present invention.

The lower area of side wall 39 is provided with an attachment mechanism, shown as internal flange 18 that enables the upper reservoir 15 to easily be assembled with lower housing 20. The lower section of the interior surface of reservoir 15, bottom wall 41, is configured with an outlet port 12 with an attached conduit or tube 13 that provides a passageway for the volatile material 11 toward the lower housing 20. Tube 13 is provided with a controlling mechanism or valve 16 to control the flow of the volatile material through tube 13. A valve adjustment mechanism 14 is attached to valve 16 to enable a user to easily adjust the flow of the volatile material 11. The valve 16 and valve adjustment mechanism 14 can be any internal or external flow control valve as is known in the art, for example needle valves, pinch valves, or stopcock-type valves, but is shown here as a clamp on valve 16 that is positioned around tube 13. When valve adjustment mechanism 14 is rotated, the clamp is tightened on the outside of tube 13, thereby restricting the interior passageway of tube 13 to cause a reduction in the flow rate of volatile material 11. Valve adjustment mechanism 14 is moveable at least between a first position and a second position, but preferably may be moveable among numerous available positions.

At the time of manufacture, a wrapping or protective cover 25 is placed over the end of tube 13 to prevent the volatile material 11 from flowing out of tube 13 until the consumer wishes to use the volatile material dispensing device 10. Protective cover 25 (best seen in FIG. 4) is attached to tear-off tab 27. The volatile material dispensing device 10 is activated when the consumer initiates the flow of volatile material 11 by manually removing the protective cover 25 from the end of tube 13 by pulling on tear-off tab 27.

The volatile material 11 flows by gravity feed past valve 16 to the end of tube 13 where it drips downward and is received by pad 24. Pad 24 is impregnated by the volatile material 11 at an appropriate, constant drip rate as determined by valve 16 in conjunction with valve adjustment mechanism 14. Then the volatile material 11 evaporates at a steady rate to permeate the atmosphere. Pad 24 is centrally located on the interior surface of base 26 of lower housing 20, being attached by any customary means, such as by glue or other adhesive material. Pad 24 may be formed of any porous material, such as foam, woven or non-woven fabric, or any other absorbent material.

Housing 20 is formed by base 26 and housing wall 21. Housing wall 21 has an attachment mechanism 23 that can be engaged with internal flange 18 to allow reservoir 15 to be attached to housing 20 for convenience of assembly of the manufactured pieces. Wall 21 is preferably designed with one or more vents 28 configured to allow for air circulation or air turbulence to encourage evaporation of the volatile material. Wall 21 is configured with at least one vertically extending slot 31 to allow the valve adjustment mechanism 14 and tear-off tab 27 to extend beyond the housing wall 21 so the consumer can access them. Two vertically extending slots 31, 38 are shown (best seen in FIG. 4). Tear-off tab 27 and valve adjustment mechanism 14 are each preferably positioned in one of slots 31, 38.

Preferably, for ease of production, volatile material dispensing device 10 is made in an upper and lower part. The upper part includes reservoir 15 with attached tube 13, valve 16, valve adjusting device 14, cover 25, and tear-off tab 27. In the manufacturing process, reservoir 15 is filled with volatile material 11 through fill point 29, and then fill point 29 is sealed, preferably by a heat seal. Then reservoir 15 is joined to lower housing 20 by engaging the lower housing attachment mechanism 23 with internal flange 18.

Figure 4:
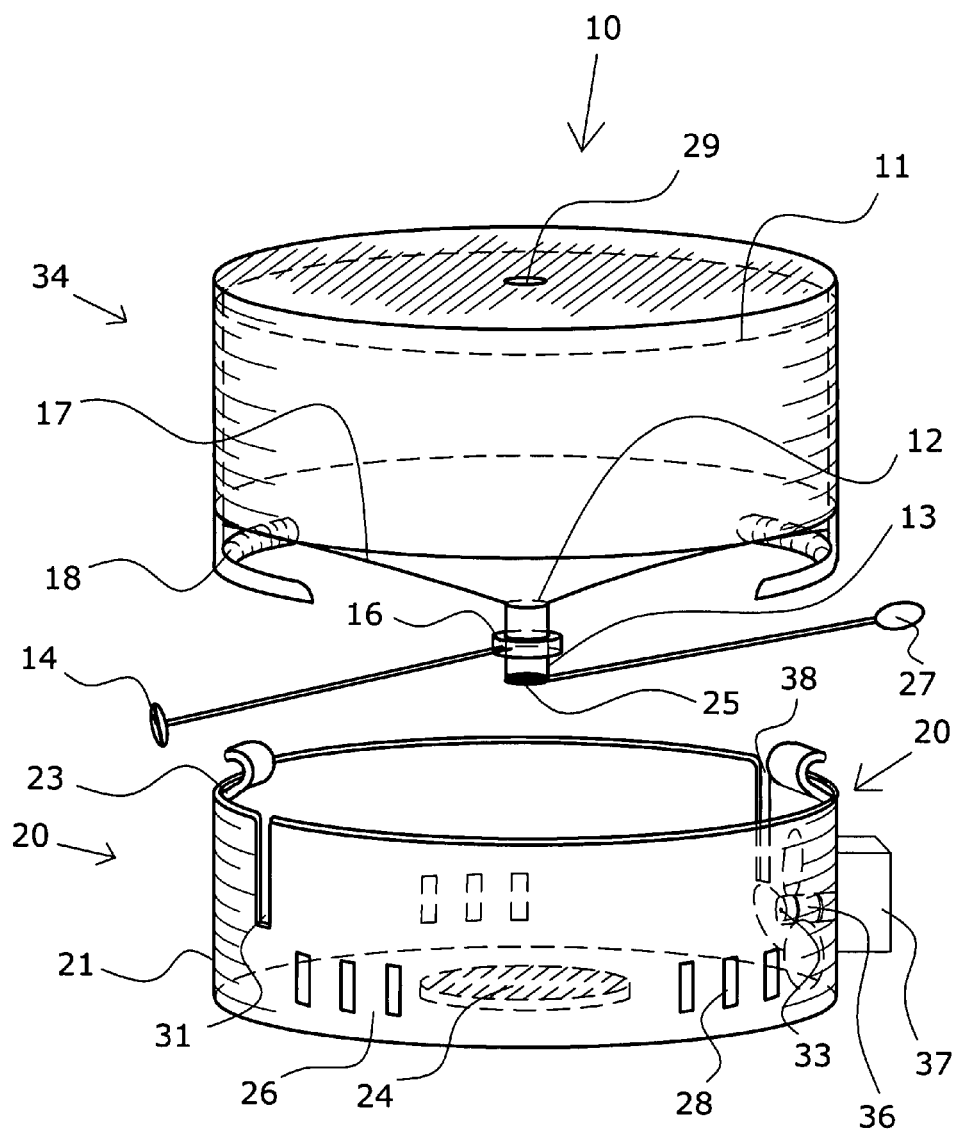
FIG. 4 is an exploded perspective view of a second preferred embodiment of the volatile material dispensing device of the present invention.

FIG. 4 shows a second embodiment that includes the features of the first embodiment with the addition of an active dispersal mechanism, shown as rotor or fan 33 and its associated wiring and power supply. Fan 33 encourages more airflow around and over pad 24 to enable faster evaporation of volatile material 11. Fan 33 is provided necessary wiring and power, shown as battery pack 37 attached to support and wiring structure 36, but alternatively fan 33 could be provided with the necessary wiring and hardware to plug into a typical household electrical outlet and configured to use standard household alternating current power. Additionally, instead of having the upper portion and the lower portion of volatile material dispensing device 10 assembled at manufacture, the upper part, including reservoir 15 with attached tube 13, valve 16, valve adjusting device 14, cover 25 and tear-off tab 27, could be produced and sold as a replaceable cartridge 34. The consumer would install cartridge 34 in a housing 20. Alternatively, volatile material dispensing device 10 can be designed with one or more attachments that are complementary to the attachment points of conventional aroma dispensers, therefore being configured to be utilized in any other conventional dispenser housing as is known in the art.

Volatile material dispensing device 10 may be economically made of synthetic plastic or other suitable material. Although illustrated in a generally circular form, in practice, reservoir 15 and lower housing 20 may be in other geometric forms and may, for example, be oval or cuboidal. Volatile material dispensing device 10 may be freestanding and moveable or may be designed to attach with an adhesive being applied either on the lower surface of lower housing 20, on the back wall of battery pack 37, or on a flattened section of the side wall 21 of lower housing 20 or side wall 39 of reservoir 15. Alternatively, a hook or eye for hanging could be molded in the area of fill point 29 to allow volatile material dispensing device 10 to be hung by a string or chain.

In both embodiments of the present invention as valve 16 is regulated in response to the manual adjustment of valve adjustment mechanism 14, control is exerted over the amount of volatile material that flows out of tube 13 and is received by pad 24. This control thereby enables the user to determine the amount of volatile material available on pad 24 for evaporation, and consequently the intensity of the vapor produced. Additionally, once manually adjusted with valve adjustment mechanism 14, the device provides an automatic time-released method of dispersal. The flow rate is continuous over time; therefore the amount of volatile material impregnating pad 24 and evaporating is constant and the intensity of the vapor produced is constant over time, as shown in FIG. 2.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

I claim:

1. A device for supplying volatile materials to be dispensed into the atmosphere, comprising:
    a reservoir having an interior surface defining a cavity and defining an outlet port;
    at least one volatile material contained in said cavity;
    a tube coupled to said outlet port in fluid communication with said cavity and configured to allow passage of said at least one volatile material;
    a valve coupled to said tube and configured to control the flow of the said at least one volatile material through said tube;
    a valve adjustment mechanism being moveable between at least a first position and a second position;
    a lower housing having an interior surface, said lower housing configured with one or more vents configured to allow air circulation; and
    a pad attached to said interior surface of said lower housing to receive said at least one volatile material.

2. The device for supplying volatile materials to be dispensed into the atmosphere as recited in claim 1 wherein said at least one volatile material comprises scented oil.

3. The device for supplying volatile materials to be dispensed into the atmosphere as recited in claim 1 wherein said at least one volatile material comprises a volatile organic compound.

4. The device for supplying volatile materials to be dispensed into the atmosphere as recited in claim 1 wherein said at least one volatile material comprises a disinfectant.

5. The device for supplying volatile materials to be dispensed into the atmosphere as recited in claim 1 wherein said at least one volatile material comprises a pest control chemical.

6. The device for supplying volatile materials to be dispensed into the atmosphere as recited in claim 1 wherein said lower housing further comprises one or more vertically disposed slots, wherein one of said one or more vertically disposed slots is configured to receive said valve adjustment mechanism.

7. The device for supplying volatile materials to be dispensed into the atmosphere as recited in claim 6 further comprising a tear-off tab, and wherein one of said one or more vertically disposed slots is configured to receive said tear-off tab.

8. The device for supplying volatile materials to be dispensed into the atmosphere as recited in claim 7 wherein said lower housing further comprises a fan mounted in said lower housing.

9. The device for supplying volatile materials to be dispensed into the atmosphere as recited in claim 8 wherein said lower housing further comprises power means electrically connected to said fan and configured to power said fan.

10. The device of claim 9 wherein said power means comprises a battery.

11. The device of claim 9 wherein said power means comprises standard household alternating current.

12. An aroma dispensing device for delivering volatile materials at a constant rate for atmospheric dispersal, comprising:
    a reservoir comprising a top, a bottom wall, and at least one reservoir side wall, said reservoir having an interior surface defining a cavity and defining an outlet port;
    a lower housing comprising at least one lower housing side wall and a base, said base having an interior surface, said at least one lower housing side wall configured with one or more vents configured to allow air circulation and configured with two vertical slots;
    at least one volatile material contained in said cavity;
    a tube having an upper section coupled to said outlet port and having a lower section extending downward into said lower housing, said tube providing fluid communication between said cavity and said lower housing, said tube configured to allow passage of said at least one volatile material;
    a valve coupled to said tube and configured to control the flow of the said at least one volatile material through said tube;
    a valve adjustment mechanism disposed in one of said two vertical slots of said at least one lower housing side wall being moveable between at least a first position and a second position;
    a pad attached to said interior surface of said base, said pad configured to receive said at least one volatile material; and
    a tear-off tab disposed in one of said two vertical slots of said at least one lower housing side wall, said tear-off tab extending from said lower section of said tube to the exterior of said lower housing, said tear-off tab configured to removably cover said lower section of said tube.

13. The aroma dispensing device for delivering volatile materials at a constant rate for atmospheric dispersal as recited in claim 12, wherein said lower housing further comprises a fan mounted in said lower housing and comprises a power means electrically connected to said fan and configured to power said fan.

14. The aroma dispensing device for delivering volatile materials at a constant rate for atmospheric dispersal as recited in claim 13 wherein said power means comprises a battery.

15. The aroma dispensing device for delivering volatile materials at a constant rate for atmospheric dispersal as recited in claim 13 wherein said power means comprises standard household alternating current.

16. The aroma dispensing device for delivering volatile materials at a constant rate for atmospheric dispersal as recited in claim 13, wherein said at least one volatile material comprises a scented oil.

17. The aroma dispensing device for delivering volatile materials at a constant rate for atmospheric dispersal as recited in claim 13, wherein said at least one volatile material comprises a volatile organic compound.

18. The aroma dispensing device for delivering volatile materials at a constant rate for atmospheric dispersal as recited in claim 13, wherein said at least one volatile material comprises a disinfectant.

19. The aroma dispensing device for delivering volatile materials at a constant rate for atmospheric dispersal as recited in claim 13, wherein said at least one volatile material comprises a pest control chemical.

20. The aroma dispensing device for delivering volatile materials at a constant rate for atmospheric dispersal as recited in claim 13, wherein said reservoir further comprises an internal flange and wherein said lower housing further comprises an attachment mechanism configured to be engaged with said internal flange, whereby said reservoir can be attached to said lower housing.

* * * * *